United States Patent
Tourrel et al.

(10) Patent No.: US 9,884,188 B2
(45) Date of Patent: Feb. 6, 2018

(54) COIL ASSEMBLY IN AN IMPLANTABLE MEDICAL DEVICE

(71) Applicant: Oticon Medical A/S, Smørum (DK)

(72) Inventors: Guillaume Tourrel, Smørum (DK); Nicolas Veau, Smørum (DK)

(73) Assignee: OTICON MEDICAL A/S, Smorum (DK)

( * ) Notice: Subject to any disclaimer, the term of this patent is extended or adjusted under 35 U.S.C. 154(b) by 0 days.

(21) Appl. No.: 14/944,487

(22) Filed: Nov. 18, 2015

(65) Prior Publication Data
US 2016/0136426 A1 May 19, 2016

(30) Foreign Application Priority Data
Nov. 19, 2014 (EP) .................................... 14193827

(51) Int. Cl.
| A61N 1/00 | (2006.01) |
| A61N 1/36 | (2006.01) |
| H02J 5/00 | (2016.01) |
| H02J 7/02 | (2016.01) |
| H02J 7/00 | (2006.01) |
| A61N 1/05 | (2006.01) |
| A61N 1/378 | (2006.01) |
| A61N 1/372 | (2006.01) |

(52) U.S. Cl.
CPC ....... *A61N 1/36032* (2013.01); *A61N 1/0541* (2013.01); *A61N 1/3787* (2013.01); *A61N 1/37217* (2013.01); *A61N 1/37229* (2013.01); *H02J 5/005* (2013.01); *H02J 7/0042* (2013.01); *H02J 7/025* (2013.01)

(58) Field of Classification Search
CPC .......................... A61N 1/36032; A61N 1/0541
USPC .......................................................... 607/61
See application file for complete search history.

(56) References Cited

U.S. PATENT DOCUMENTS

| 6,505,077 B1 * | 1/2003 | Kast ......................... A61N 1/08 607/61 |
| 2005/0075700 A1 | 4/2005 | Schommer et al. |
| 2005/0245985 A1 | 11/2005 | Deininger et al. |
| 2009/0018600 A1 | 1/2009 | Deininger et al. |
| 2011/0009924 A1 | 1/2011 | Meskens |
| 2014/0155686 A1 | 6/2014 | Meskens |

* cited by examiner

*Primary Examiner* — Nadia A Mahmood
(74) *Attorney, Agent, or Firm* — Birch, Stewart, Kolasch & Birch, LLP

(57) ABSTRACT

According to an embodiment, a receiver coil assembly for an implantable medical device is disclosed. The receiver coil assembly includes at least two spatially separated coil units comprised by a housing of an internal component. The spatial separation is along a thickness of the housing.

20 Claims, 3 Drawing Sheets

COIL ASSEMBLY IN AN IMPLANTABLE MEDICAL DEVICE

FIELD

The disclosure relates to an implantable medical device. More particularly, the disclosure relates to a receiver coil assembly for the implantable medical device such as a cochlear implant.

BACKGROUND

Wireless transmission of data and power has emerged as a popular and essential characteristic of implantable medical devices such as cardiac pacemakers, implantable cardioverter defibrillators, recording devices, neuromuscular stimulators, prosthetic devices such as cochlear implants. Inductive coupling is popular and effective means to realize transcutaneous link for implanted biomedical devices because a coil pair may be used both for data as well as power transmission to the implanted circuitry.

Implantable prosthesis devices are generally required to be small to reduce the trauma and other complications arising from the implantation and maintenance of foreign matter inside a patient's body. For example, a cochlear implant typically include an external component and an internal component. The external component is external to the patient's body whereas the internal component is implanted in the patient's body.

The external component includes a microphone for sensing ambient sounds and a signal processor for generating processed electrical signals corresponding to these sounds. The processed electrical signals are transmitted, using a transmitter coil of the external component, to the internal component that applies the same to the auditory nerve of the patient through an array of electrodes. Because the internal component may not have a permanent power supply, power for the component is also derived from the external component. The means for providing both power and communication between the internal and external components is typically a pair of coils, the transmitter coil in the external component and a receiver coil in the internal component. The coils are generally planar and are positioned parallel to each other so that energy is coupled through the skin and flesh of the patient from the transmitter coil to the receiver coil for the purpose of powering and/or controlling the internal component.

FIG. 1A illustrates an electromagnetic coupling in a conventional cochlear implant. The cochlear implant 100 works on the principle of the external component 102 being coupled to an internal component 104 via an electromagnetic inductive coupling 106. The purpose is to activate auditory nerve 126 by using an electrode array placed in cochlea 124, thus allowing profoundly deaf patients (i.e., those whose middle and/or outer ear is dysfunctional, but whose auditory nerve remains intact) to hear again.

Referring now to FIG. 1B that illustrates a schematic diagram of the external component 102 and the internal component 104 in the conventional cochlear implant. The external component 102 includes a microphone or a multi-microphone assembly 110, a signal processor 112, an energy source 114 and a transmitter coil 116. The microphone or multi-microphone assembly 102 picks up an audio sound 108 from patient's environment and converts the audio sound into electrical signals. The signal processor 112 processes the electrical signals to generate the processed electrical signals, typically a sequence of pulses of varying width and/or amplitude. The processed electrical signals, once generated, are transmitted to a stimulation electronics 120 of the internal component 104 via the inductive link 106 established between the transmitter coil 116 and a receiver coil 118. The stimulation electronics 120, in response to receipt of the processed electrical signals, generates appropriate pulses of stimulating electrical signals that are applied to one or more electrodes of an electrode array 122 that is inserted into the cochlea 124 of the patient. It is the stimulating electrical signals that directly stimulate the auditory nerve 126 and provides the patient with the sensation of hearing.

FIG. 1C shows the internal arrangement of elements in the internal component in a partial cross section view of a conventional cochlear implant. The internal component 104 includes an implantable hermetical housing 128. The implantable hermetic housing 128 includes the stimulation electronics 120, the receiver coil 118 and a magnet 130 for the external antenna holding. The magnet 130 is used to hold and align the receiver coil 118 with the transmitter coil (FIG. 1 B, 116) of the external component (FIG. 1 B, 102) directly over the location where the receiver coil 118 associated with the implanted stimulation electronics 120 is located. Typically, the housing includes a ceramic body 136 hermetically closed with a flat titanium cover 132. The housing further includes feedthroughs 134. The feedthroughs 134 provide an electrically conducting path extending from interior of a hermetically sealed housing, to an external location outside the housing. This arrangement allows one or more electrical connections to be made between the electrode array (FIG. 1 B, 122) and the stimulation electronics (FIG. 1B, 120) within the hermetically sealed housing, whilst protecting the circuitry or other hermetically sealed elements from any damage or malfunction that may result from exposure to the environment surrounding the housing.

Placing the receiver coil 118 with the stimulation electronics 120 inside the hermetic housing is typically preferred because of the material that may be used for the coil. For example an insulated copper wire, considered to be a preferable material for coil, may be used for manufacturing the receiver coil. However, this results in a decrease in distance d between the receiver coil 118 and the metallic component such as titanium cover 132. The metallic component 132 typically is a distal surface from skin of the patient when the housing 128 is in implanted position. This distance d is a major factor for determining performance of the inductive link. When the distance d between the hermetically sealed receiver coil 118 and the metallic components 132 is small, the inductive link performance between the transmitter coil 116 and the receiver coil 118 is poor partly because the receiver coil 118 is further away from the transmitter coil 116. In fact, the proximity of the receiver coil 118 to the metallic component 132 results in undesirable magnetic interferences, negatively affecting the inductive link yield. Therefore, when the distance d decreases, the performance of the inductive link decreases too.

Therefore, there is a need to provide an alternative solution that overcomes the shortcomings of the existing solutions.

SUMMARY

The disclosed configuration of a receiver coil assembly improves performance of the inductive link between a transmitter coil and a receiver coil assembly in the implantable medical device such as a cochlear implant. The disclosed coil configuration, along with a better inductive performance, may further allow keeping the internal component of the implantable medical device compact.

The inductive link performance is defined as the data and/or power transfer efficiency of the inductive link established between the transmitter coil usually of an external component and the receiver coil assembly of the internal implanted component.

According to an embodiment, a receiver coil assembly for an implantable medical device is disclosed. The receiver coil assembly includes at least two spatially separated coil units comprised by a housing of an internal component. The spatial separation is along a thickness of the housing. The at least two spatially separated coil units includes an external coil and an internal coil.

The external coil includes at least one coil winding. The external coil may be engraved or assembled on a proximal surface of the housing. The proximal surface of a ceramic body of the housing acts as a substrate for positioning the external coil. The proximal surface is the side that is closer to skin of the patient when the internal component is in implanted positioned.

The ceramic body may be made up of alumina, zirconia, Zirconia Toughened Alumina (ZTA) or Yttria Tetragonal Zirconia Polycrystal (YTZP).

The external coil may be made of a conducting material such as platinum or pure gold.

In an embodiment, the external coil is not encapsulated within the hermetically sealed housing. Instead, the external coil may be covered with an insulation layer made of a biocompatible material such as parylene, Polyether ether ketone (PEEK), or a think ceramic layer. This allows for protecting the external coil against surrounding body tissues and liquid.

The positioning of the external coil on the proximal side places the external coil closer to the transmitter coil, thus improving the inductive link performance. It would be apparent to the skilled person that placing the external coil as close as possible to the transmitter coil would improve the inductive link performance. Therefore, it is possible to place the external coil at a position other than the proximal surface if such positioning allows for an increase in the inductive link performance.

In one embodiment, the external coil is assembled over the proximal surface. The assembling provides more flexibility in placing the internal coil. In another embodiment, the external coil is engraved over the proximal surface. Engraving provides a manufacturing method with relatively more consistent results in arrangement of the external coil.

The internal coil includes at least one coil winding. The internal coil may be printed or assembled on an inner surface of the housing or on a hermetically sealed component of the housing. The inner surface of the housing is a surface that is encapsulated within the hermetically sealed housing. The hermetically sealed components include components of the internal component that are encapsulated within the hermetically sealed housing. This may include the stimulation electronics that is adapted to receive the processed electrical signals using the receiver coil assembly and to generate the stimulating electrical signals. The hermetically encapsulated internal coil allows for preventing the internal coil from any damage that may result from exposure to the environment surrounding the housing.

In one embodiment, the internal coil is a component that is positioned assembled on the inner surface or the hermetically sealed component. The assembling provides more flexibility in placing the internal coil. In another embodiment, the internal coil is directly printed or metallized on the inner surface or the hermetically sealed component. Printing or metallizing provides a manufacturing method with relatively more consistent results in arrangement of the internal coil.

In an embodiment, the internal coil is made up of copper. Additionally or alternatively, the external coil may be made up of copper.

In an embodiment, the internal coil is hermetically sealed within the housing and is proximal to a stimulation electronics relative to the external coil.

In an embodiment, the external coil is covered with the biocompatible layer and is proximal to the transmitter coil relative to the internal coil.

In an embodiment, the relative positioning of the internal coil and the external coil satisfies a predetermined criterion. The predetermined criterion includes positioning the internal coil and the external coil such that a first distance between the external coil and a metallic cover of the housing is more than a second distance between the internal coil and the metallic component of the housing. The metallic cover is typically on distal side of the housing, the distal side being further away from the skin of the patient relative to the proximal surface. In an embodiment, the distance between the metallic component and the external coil is increased at least by the thickness of the ceramic body.

In an embodiment, the external coil and the internal coil are independent of each other. The term "independent" is defined as the internal coil and the external coil not being coupled to each other and are independently connected to the stimulation electronics. This allows the stimulation electronics to individually receive the processed electrical signals from the individual coil units, i.e. external coil and internal coil. In an embodiment, for example for a cochlear implant, each coil may be adapted to receive data information corresponding to different frequency ranges. This may be implemented where the external coil is adapted to receive data information corresponding to high frequency sound information and the internal coil is adapted to receive data information corresponding to low frequency sound information.

In another embodiment, one of the external coil or the internal coil is adapted to receive energy from a transmitter coil connected to a power supply and another of the external coil or the internal coil is adapted to receive data from a transmitter coil connected to a data source.

In an embodiment, one of the external coil or the internal coil is adapted to receive energy from a transmitter coil connected to a power supply, the received energy corresponding to the application specific energy; and another of the external coil or the internal coil is adapted to receive additional energy from the transmitter coil connected to the power supply, the additional energy being a reserve energy for accommodating instantaneous energy demand of the application. The application specific energy may vary from type of application of the receiver coil assembly. For example, for a cochlear implant, where the receiver coil assembly is implanted within the patient, the application specific energy corresponds to the energy required for producing electrical stimulation for a predefined frequency range in order to generate sound perception, which defines the application. The additional energy may be stored in a storage component within the housing for accommodating instantaneous energy demand. This allows for making additional energy demand addressed locally within the housing instead of relying on power transmitted using the transmitter coil for such instantaneous energy demands.

Wider bandwidth and high data rates are better supported at higher frequency and efficient power transfer typically achieved better using low operating frequency. Therefore, the internal coil and external coil may individually be used for separate applications, such as power transfer and data transfer.

Alternatively, in another embodiment, the external coil and the internal coil are coupled together.

According to an embodiment, an implantable receiver coil assembly for an implantable medical device is disclosed. The receiver coil includes an external coil and an internal coil, the external coil and the internal coil being spatially separated coil units and comprised by a housing of an internal component, the spatial separation being along a thickness of the housing, wherein an insulated wire follows shape of the housing to connect the external coil to a hermetically sealed electronic circuitry comprised within the housing.

Following the shape may be defined where the insulated wire runs along the inner periphery of the (axial) thickness of the housing while being affixed to the inner surface. Following the shape of the housing allows for utilizing otherwise limited space of the housing efficiently and avoiding the insulated wire being entangled with other components in the housing.

In one embodiment, following shape of the housing comprises the insulated wire running from the external coil along an inner periphery, corresponding to thickness of the housing, to the hermetically sealed electronic circuitry. Additionally, the inner periphery, along its thickness, may further include a groove path comprising a depth such that the insulated wire, running within the groove path, is flush with surface of the inner periphery. Placing the insulated wire in the depth of the groove path such that the insulated wire is flush with the surface allows for utilizing radial thickness of the housing allows for even better utilization of the limited volumetric space of the housing. Alternatively the groove path is provided with a cover adapted to enclose the insulated wire within the groove depth, the cover conforming to shape of and flush with inner periphery of the housing. This provides further protection to the insulating wire.

In an embodiment, the external coil is connected to a hermetically sealed electronic circuitry using insulated wires. The insulated wires may follow shape of the housing. In one embodiment, following the shape of the housing is illustrated by having the wires run from the external coil, at least along periphery corresponding to the thickness of the housing, to the encapsulated stimulation electronics. In another embodiment, following the shape includes the insulating wires being running at least along a groove that is sandwiched between walls of the periphery corresponding to the thickness of the housing. Such arrangement of having the insulated wires following shape of the housing allows for an optimal utilization of housing geometry and space within the housing. In either embodiments, the insulated wires may also run along the parallel or substantially parallel to the proximal surface and/or the distal side.

Although the implantable device may include any of the cardiac pacemakers, implantable cardioverter defibrillators, recording devices, neuromuscular stimulators, prosthetic devices like retinal implants. However, in a specific embodiment, the implantable medical device is a cochlear implant. The implantable medical device includes the receiver coil assembly, which operates as a receiver coil of the internal component of the cochlear implant. The receiver coil assembly is adapted to inductively link with the transmitter coil associated with an external sound processor of the cochlear implant.

In an embodiment, the thickness of the internal component of the cochlear implant is approximately 5 mm or less.

In an embodiment, an internal component representing implantable part of an implantable medical device is disclosed. The internal component includes a receiver coil assembly adapted to inductively receive a processed electrical signals. The receiver coil assembly includes at least two spatially separated coil units comprised by a housing of the internal component. The spatial separation is along a thickness of the housing. The internal component further includes a stimulation electronics adapted to receive the processed electrical signal from the receiver coil assembly and to generate stimulating electrical signals for an electrode array implanted in a tissue targeted for stimulating a bodily part.

In an embodiment, the internal component is the implanted part of the cochlear implant and the electrode array is positioned within cochlea of the patient in order to activate the auditory nerve.

The skilled person would realize that the above-disclosed internal component of the embodiment may include any feature of the disclosed receiver coil assembly. For example, a first distance between the external coil and a metallic cover of the housing of the internal component is more than a second distance between the internal coil and the metallic component of the housing. Other implementations using combination of one or more features of the receiver coil assembly are also within the scope of the disclosure.

In an embodiment, the receiver coil is adapted to be implanted within a patient and is adapted to be coupled to an implanted battery, the implantable battery being adapted to provide application specific energy. The receiver coil assembly is connected to the hermetically sealed electronic circuitry, which is adapted to determine charge level of the implanted battery and to initiate a charging stage if the determined charge level drops below a predetermined threshold value. The predetermined threshold value is usually set in accordance to the application specific energy requirement. During charging stage of the implanted battery, both the external coil and internal coil are adapted to receive energy from a transmitter coil connected to an external power supply and to provide the received energy for charging the implanted battery. Thus, utilizing both coil instead of one during the charging process allows for quicker charging of the implanted battery. For a cochlear implant, this is particularly useful if during the charging time, the user is not exposed to sound of interest such as during sleeping using a charging sleeping pillow providing external power supply.

In an embodiment, the receiver coil assembly is adapted to be implanted within a patient and is adapted to be coupled to an implanted battery, the implanted battery being adapted to provide application specific energy. The receiver coil assembly is connected to a hermetically sealed electronic circuitry adapted to determine charge level of the implanted battery and to perform a battery decoupling if the determined charge level drops below a predetermined threshold value. The predetermined threshold value is usually set in accordance to the application specific energy requirement. The battery decoupling is defined as prior to decoupling one of the coils was being used to inductively receive power from the implanted battery and post decoupling, such inductive receiving of power from the implanted battery using one of the coils of the receiver coil assembly is stopped. After the battery decoupling, one of the external coil or the internal coil is adapted to receive energy from a transmitter coil connected to an external power supply and another of the external coil or the internal coil is adapted to receive data from the transmitter coil connected to a data source. Thus, for a cochlear implant, the combination of utilizing an implanted battery and external power source using the disclosed receiver coil assembly allows for flexibility in usage of the cochlear implant.

In one embodiment, a cochlear implant is disclosed. The cochlear implant includes an external component comprising a microphone adapted to receive an audio sound. The microphone is also adapted to generate an electrical signal corresponding to the audio sound. The external component further includes a signal processor adapted to process the electrical signal and generating a processed electrical signal, and a transmitter coil adapted to transmit the processed electrical signal. The cochlear implant further includes an internal component that includes a receiver coil assembly adapted to receive the processed electrical signals. The receiver coil assembly includes at least two spatially separated coil units comprised by a housing of an internal component. The spatial separation is along a thickness of the housing. The internal component further includes a stimulation electronics receiving the processed electrical signal from the receiver coil assembly and generating stimulating electrical signals for an electrode array positioned within cochlea of a patient.

In one embodiment, an internal coil axis of the internal coil and an external coil axis of the external coil are misaligned or offset with respect to each other. The definition of coil axis is known in the art, for example from axis of a circular planar coil carrying current.

In an embodiment, the external coil is moveable such that an external coil axis is adjustable for controlling inductive coupling with a transmitter coil. In this embodiment, the insulating wire, connecting the external coil with the hermetically sealed electronic circuitry, comprises extra length proximal to the external coil before the insulating wire follows the shape of the inner periphery. The extra length of the insulating wire is adapted to provide extension in accordance with adjustment of the external coil axis. The movement of the coil such as by tilting might move the connection point between the external coil and insulating wire away from the point where the wire starts following the shape of the inner periphery. The extra length ensures that integrity of the connection between the external coil and the insulated wire is maintained despite the movement of the external coil.

In an embodiment, the external coil is provided on a plate member at proximal surface of the housing. The plate member is adapted to rotate or tilt around a pivot axis in response to a command. The pivot axis is typically same as the external coil axis. Thus, the external coil may be rotated or tilted so that the external coil is in alignment with the transmitter coil, thus increasing efficiency of the inductive link. The electronic circuitry may be adapted to monitor the link efficiency and in response to the link efficiency below a threshold value, the electronic circuitry may be adapted to send a command to rotate or tilt the external coil. Alternatively, a user may provide an instruction, for example using a remote control like a smartphone, that is inductively transmitted to the electronic circuitry using the transmitter coil-receiver coil assembly set up. In response, the electronic circuitry may provide the command to the external coil to rotate or tilt the external coil.

In an embodiment, the plate member is positioned over a pivotable module that is adapted to be rotate or tilt around the pivot axis. The pivot axis is typically same as the external coil axis. The pivotable module is adapted to be driven by an implanted motor that is adapted to receive command from the hermetically sealed electronic circuitry, and to be locked in a predetermined orientation of external coil axis. The predetermined orientation is typically defined by alignment between the transmitter coil and the external coil. The locking may be provided by known pivot joint locking techniques at different tilt angles.

In a use scenario, where a microphone capable to capturing ambient sound and providing a microphone signal for the application (sound perception using cochlear implant) is positioned within an ear canal of a user, the external ear canal may be oriented towards the ear canal such that the external coil is aligned with a transmitter coil associated with transmission of the microphone signal.

In an embodiment, a cochlear implant comprising the disclosed receiver coil assembly is provided.

In an embodiment, the cochlear implant comprising the disclosed receiver coil assembly includes an external component and an implantable hermetically sealed electronic circuitry. The external component includes an external component comprising a microphone adapted to receive an audio sound and generate an electrical signal corresponding to the audio sound, a signal processor adapted to process the electrical signal for generating a processed electrical signal, and a transmitter coil adapted to inductively transmit the processed electrical signal to the receiver coil assembly. The implanted hermetically sealed electronic circuitry adapted to receive the processed electrical signal using the receiver coil assembly and generating stimulating electrical signals for an electrode array positioned within cochlea of a patient.

In an embodiment, the external component comprises a modulator to modulate the processed electrical signal; and the internal component includes electronic circuitry including a demodulator adapted to demodulate the processed electrical signal to obtain data for generating the stimulation electrical signal; and a rectifier adapted to rectify the processed electrical signal to obtain power for generating the stimulation electrical signal.

In an embodiment, the cochlear implant comprising the disclosed receiver coil assembly includes an external component and an implantable hermetically sealed electronic circuitry. The external component includes a microphone adapted to receive an audio sound and generate an electrical signal corresponding to the audio sound, and a transmitter coil adapted to inductively transmit the electrical signal to the receiver coil assembly. The implantable hermetically sealed electronic circuitry adapted to receive the electrical signal using the receiver coil assembly, to process the received electrical signal for generating a processed electrical signal and generating stimulating electrical signals for an electrode array positioned within cochlea of a patient.

The disclosed cochlear implant may include any of the features described in preceding paragraphs in relation to the receiver coil assembly. For example, the at least two spatially separated coil units include an external coil and the internal coil. The external coil, including at least one coil winding, is engraved or assembled on a proximal surface of the housing. Similarly, the internal coil, including at least one coil winding, is printed or assembled on an inner surface or on a hermetically sealed component of the housing.

It would be apparent to the skilled person that other disclosed features of the receiver coil assembly may also be included in the disclosed cochlear implant.

In yet another embodiment, a method for manufacturing an internal component of an implantable medical device is disclosed. The method includes bonding an internal coil on an inner surface or on a hermetically sealed component of the housing and connecting the internal coil to a stimulation electronics. The internal coil may include at least one coil winding. The stimulation electronics is connected with a first end of a plurality of feedthroughs. A second end of the feedthroughs is made accessible outside the housing. An external coil is positioned on a proximal surface of the housing, the proximal surface being distal from the stimulation electronics relative to the internal coil. The external coil may include at least one coil winding. The external coil is then covered with a biocompatible layer. Lastly, the hermetically sealed stimulation electronics is connected to an electrode array via the second end of the plurality of feedthroughs.

The housing is hermetically sealed as part of the manufacturing method. The hermetically sealed components include components that in a manufactured internal implantable component are encapsulated within the hermetically sealed housing. Usually, the second end of the feedthroughs may be made accessible at the distal side of the housing or the circumferential periphery along the thickness of the housing.

Bonding the internal coil may include any of assembling or printing or metallizing. Positioning the external coil includes any of assembling or engraving or metallizing.

Furthermore, the method may also include connecting the external coil to a hermetically sealed electronic circuitry using insulated wires. The insulated wires may follow shape of the housing.

The skilled person would appreciate that any of the features disclosed for the receiver coil assembly and/ or disclosed cochlear implant may also be form part of the disclosed method. For example, the external coil and the internal coil are independent of each other; or coupling the external coil and the internal coil to each other. Also, the skilled person would note that some of the sequence of some of the steps in the method may be changed. For example, positioning the external coil on the proximal surface of the housing may precede bonding of the internal coil on the inner surface.

BRIEF DESCRIPTION OF ACCOMPANYING FIGURES

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other embodiments. These and other embodiments, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, steps, processes, etc. (collectively referred to as "elements").

Figure 2:
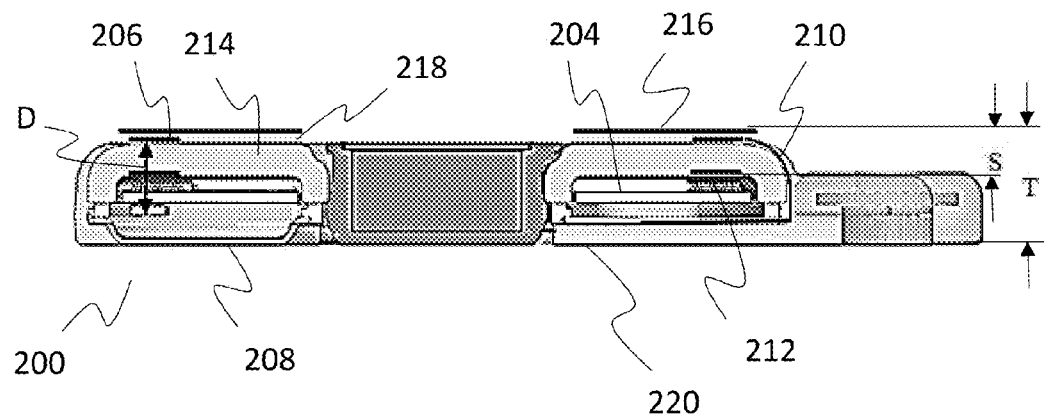
FIG. 2A shows a cross section view of the internal component with the external coil and internal coil according to an embodiment.
FIG. 2B shows a top view of an internal component of the implantable medical device according to an embodiment.
Figure 2:
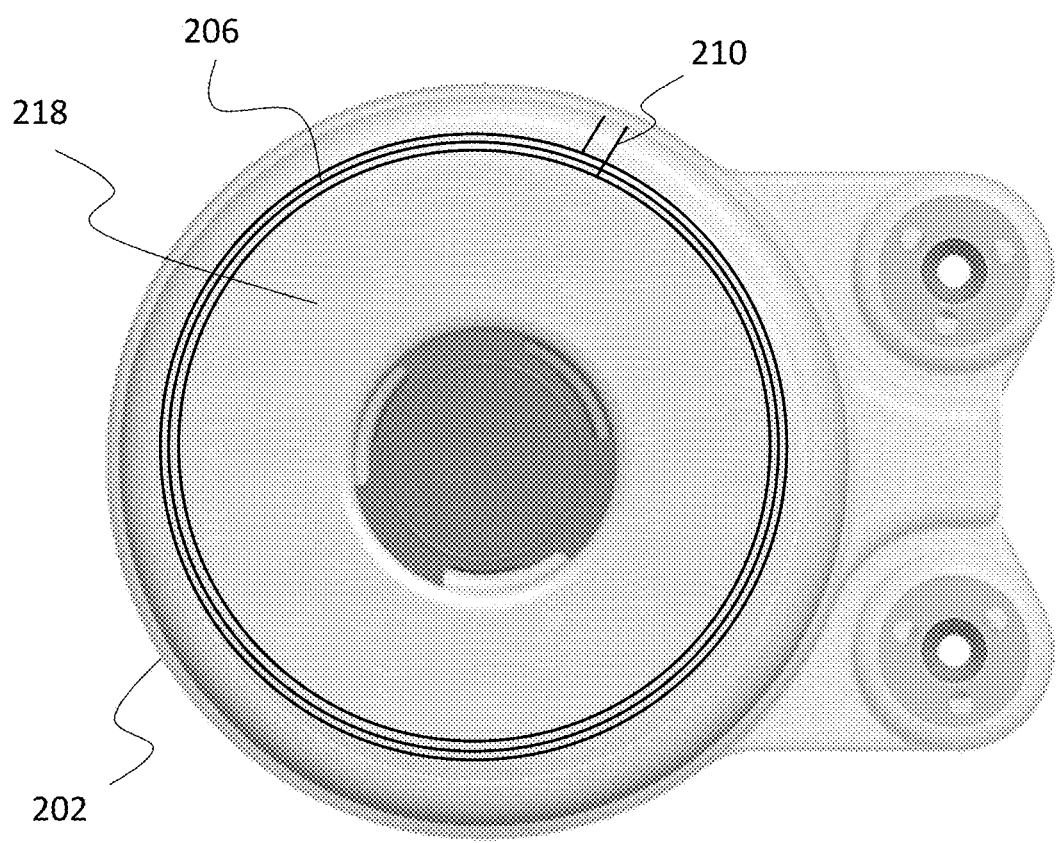

FIG. 2A shows a cross section view of the internal component with the external coil and internal coil according to an embodiment. In addition, FIG. 2B shows a top view of an internal component of the implantable medical device according to an embodiment.

The internal component 200 includes a receiver coil assembly 206, 212. The receiver coil assembly includes at least two spatially separated coil units 206, 212 comprised by a housing 202 of the internal component. The spatial separation S is along a thickness T of the housing 202.

The at least two spatially separated coil units includes an external coil 206 and an internal coil 212.

The external coil 206 includes at least one coil winding (see 206, FIG. 2B). The external coil may be engraved or assembled on a proximal surface 218 of the housing 202. The proximal surface of a ceramic body of the housing acts as a substrate for positioning the external coil. The external coil 206 may be made of a conducting material such as platinum or pure gold. The external coil is covered with an insulation layer made of a biocompatible material 216 such as parylene, Polyether ether ketone (PEEK), or a think ceramic layer. In one embodiment, the external coil 206 is assembled over the proximal surface. In another embodiment, the external coil 206 is engraved over the proximal surface 218.

The internal coil 212 includes at least one coil winding (see 212, FIG. 2A). The internal coil may be printed or assembled on an inner surface of the housing or on a hermetically sealed component of the housing 202. In an embodiment, the internal coil 212 is printed on the stimulation electronics 204. In one embodiment, the internal coil is a component that is positioned assembled on the inner surface or the hermetically sealed component. In another embodiment, the internal coil is directly printed or metallized on the inner surface or the hermetically sealed component.

In an embodiment, the internal coil 212 is hermetically sealed within the housing 202 and is proximal to a stimulation electronics 204 relative to the external coil 206.

Figure 1:
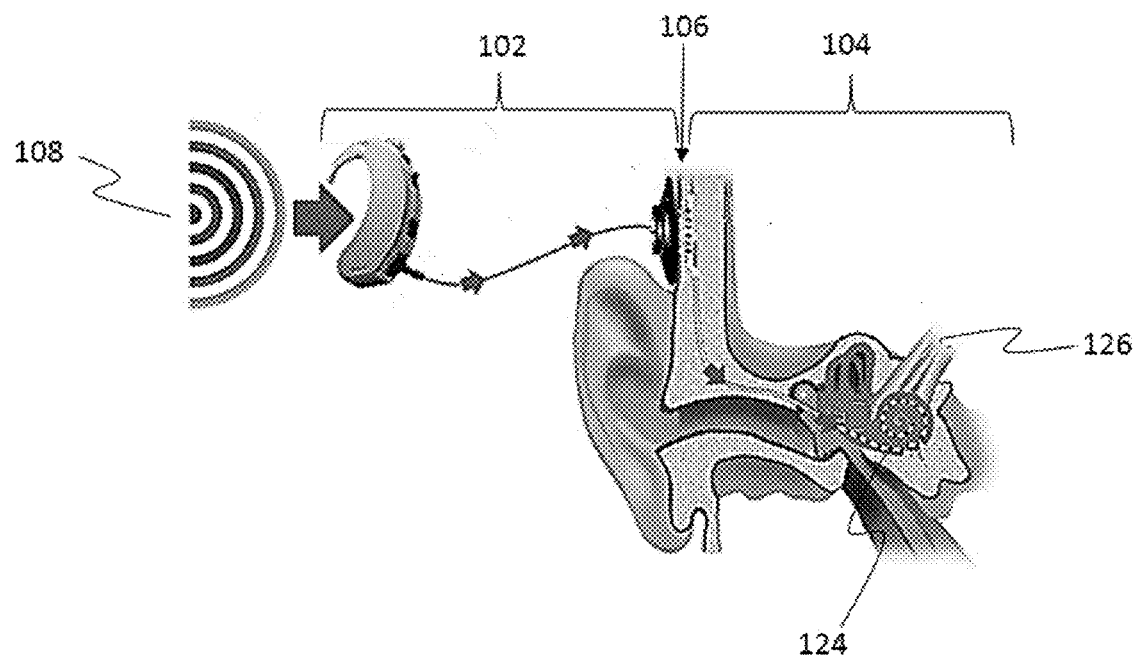
FIG. 1A illustrates an electromagnetic coupling in a conventional cochlear implant.
FIG. 1B illustrates a schematic diagram of the external component and the internal component in the conventional cochlear implant.
FIG. 1C shows the internal arrangement of elements in a partial cross section view of the internal component in a conventional cochlear implant.
Figure 1:
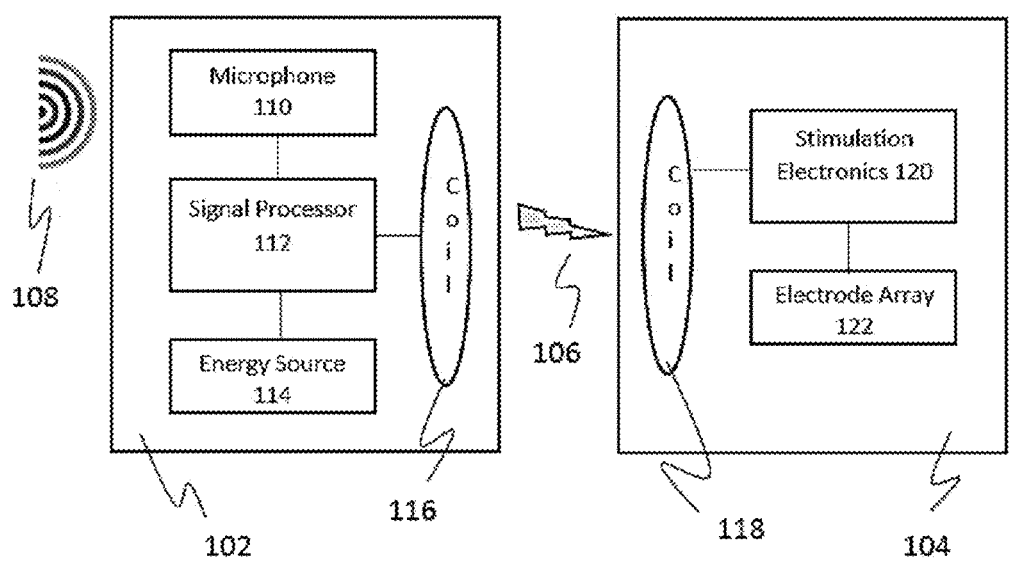
Figure 1:
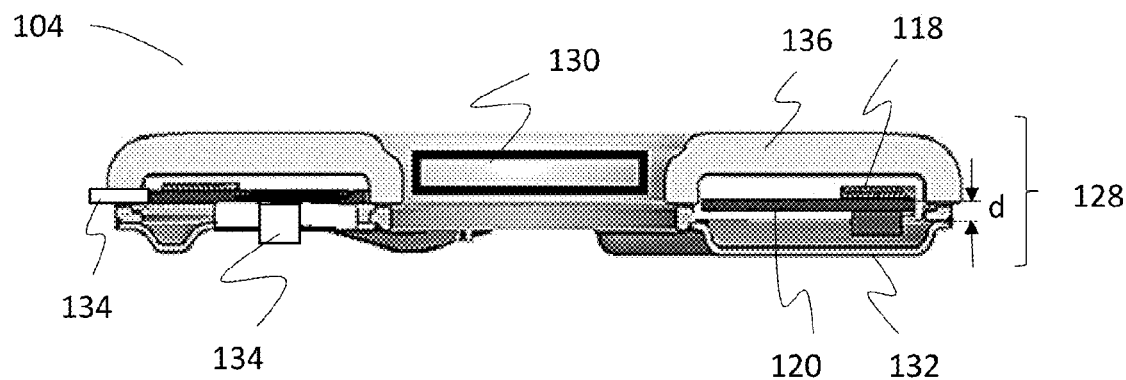

In an embodiment, the external coil 206 is covered with the biocompatible layer 216 and is proximal to the transmitter coil (see 116, FIG. 1B) relative to the internal coil 212.

In an embodiment, the relative positioning of the internal coil 212 and the external coil 206 satisfies a predetermined criterion. The predetermined criterion includes positioning the internal coil 212 and the external coil 206 such that a first distance between the external coil 206 and a metallic cover 208 such as titanium cover of the housing 202 is more than a second distance between the internal coil 212 and the metallic component 208 of the housing 202. The metallic cover 208 is typically on distal side 220 of the housing 202, the distal side being further away from the skin of the patient relative to the proximal surface. In an embodiment, the distance between the metallic component 208 and the external coil 206 is increased at least by the thickness of the ceramic body 214.

In an embodiment, the external coil 206 and the internal coil 212 are independent of each other. Alternatively, in another embodiment, the external coil 206 and the internal coil 212 are coupled together.

In an embodiment, the external coil 206 is connected to a hermetically sealed electronic circuitry 204 using insulated wires 210. The insulated wires 210 may follow shape of the housing.

In an embodiment, the implantable medical device is a cochlear implant. The implantable medical device includes the receiver coil assembly 206, 212, which operates as a receiver coil (see 118, FIG. 1B) of the internal component of the cochlear implant. The internal component is implantable within a cochlear implant user body. The receiver coil assembly is adapted to inductively link with the transmitter coil (see 118, FIG. 1B) associated with an external sound processor of the cochlear implant.

In an embodiment, an internal component 200 representing implantable part of an implantable medical device is disclosed. The internal component 200 includes a receiver coil assembly 206, 212 adapted to inductively receive a processed electrical signals. The receiver coil assembly includes at least two spatially separated coil units 206, 212 comprised by a housing 202 of the internal component 200. The spatial separation is along a thickness T of the housing 202. The internal component further includes a stimulation electronics adapted to receive the processed electrical signal from the receiver coil assembly and to generate stimulating electrical signals for an electrode array implanted in a tissue targeted for stimulating a bodily part.

In one embodiment, a cochlear implant is disclosed. The cochlear implant includes an external component (see 102, FIG. 1B) comprising a microphone (see 110, FIG. 1B) adapted to receive an audio sound (see 118, FIG. 1B). The microphone is also adapted to generate an electrical signal corresponding to the audio sound. The external component further includes a signal processor (see 112, FIG. 1B) adapted to process the electrical signal and generating a processed electrical signal, and a transmitter coil (see 116, FIG. 1B) adapted to transmit the processed electrical signal. The cochlear implant further includes an internal component 200 that includes a receiver coil assembly 206, 212 adapted to receive the processed electrical signals. The receiver coil assembly includes at least two spatially separated coil units 206, 212 comprised by a housing 202 of the internal component 200. The spatial separation S is along a thickness T of the housing. The internal component further includes a stimulation electronics 204 receiving the processed electrical signal from the receiver coil assembly and generating stimulating electrical signals for an electrode array (see 122, FIG. 1B) positioned within cochlea (see 124, FIG. 1A) of a patient.

In an embodiment of cochlear implant, the positioning of the external coil 206 allows the external coil to be closer to and facing the transmitter coil.

The internal coil 212 be connected to the electronics with a bonding technique.

The internal coils 212 and the external coil 206 may be obtained by the serigraphy with a masking procedure in order to create accurate and very narrow electrical tracks. Insulation and protection of the coils may be obtain by applying a biocompatible layer 216 using chemical vapor deposition technique, for example a parylene deposition. Insulation may also be obtained by plasma projection or ceramic powder, thus ensuring hard protection of the coil.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

Accordingly, the scope should be judged in terms of the claims that follow.

We claim:

1. A cochlear implant comprising:
an implantable receiver coil assembly comprising:
an external coil and an internal coil, the external coil and the internal coil being spatially separated coil units and comprised by a housing of an internal component, the spatial separation being along a thickness of the housing, wherein
an insulated wire is arranged to connect the external coil to a hermetically sealed electronic circuitry comprised within the housing, wherein
one of the external coil or the internal coil is adapted to receive energy from a transmitter coil connected to a power supply, the received energy corresponding to the application specific energy; and
another of the external coil or the internal coil is adapted to receive additional energy from the transmitter coil connected to the power supply, the additional energy being a reserve energy for accommodating instantaneous energy demand of the application.

2. A cochlear implant comprising:
an implantable receiver coil comprising:
an external coil and an internal coil, the external coil and the internal coil being spatially separated coil units and comprised by a housing of an internal component, the spatial separation being along a thickness of the housing, wherein
an insulated wire is arranged to connect the external coil to a hermetically sealed electronic circuitry comprised within the housing, wherein the receiver coil assembly is adapted to be implanted within a patient and is adapted to be coupled to an implanted battery, the implanted battery being adapted to provide application specific energy;

the receiver coil assembly is connected to a hermetically sealed electronic circuitry adapted to determine charge level of the implanted battery and to perform a battery decoupling if the determined charge level drops below a predetermined threshold value; and after the battery decoupling, one of the external coil or the internal coil is adapted to receive energy from a transmitter coil arranged to be connected to an external power supply and another of the external coil or the internal coil is adapted to receive data from the transmitter coil connected to a data source.

3. A cochlear implant comprising:
an implantable receiver coil assembly comprising:
   an external coil and an internal coil, the external coil and the internal coil being spatially separated coil units and comprised by a housing of an internal component, the spatial separation being along a thickness of the housing, wherein
   an insulated wire is arranged to connect the external coil to a hermetically sealed electronic circuitry comprised within the housing, wherein
an internal coil axis of the internal coil and an external coil axis of the external coil are misaligned or offset with respect to each other.

4. A cochlear implant comprising:
an implantable receiver coil assembly comprising:
   an external coil and an internal coil, the external coil and the internal coil being spatially separated coil units and comprised by a housing of an internal component, the spatial separation being along a thickness of the housing, wherein
   an insulated wire is arranged to connect the external coil to a hermetically sealed electronic circuitry comprised within the housing, wherein
the external coil is moveable such that an external coil axis is adjustable for controlling inductive coupling with a transmitter coil; and
the insulated wire, arranged to connect the external coil with the hermetically sealed electronic circuitry, comprises extra length proximal to the external coil before the insulating wire follows the shape of the inner periphery, the extra length being adapted to provide extension in accordance with adjustment of the external coil axis.

5. The cochlear implant according to claim 4, wherein the external coil is provided on a plate member at proximal surface of the housing, the plate member being adapted to rotate or tilt around a pivot axis in response to a command.

6. The cochlear implant according to claim 5, wherein the plate member is positioned over a pivotable module that is adapted to be rotate or tilt around the pivot axis, the pivotable module being adapted to be
   driven by a motor that is adapted to receive command from the hermetically sealed electronic circuitry, and
   locked in a predetermined orientation of external coil axis.

7. A cochlear implant comprising:
an implantable receiver coil assembly comprising:
   an external coil and an internal coil, the external coil and the internal coil being spatially separated coil units and comprised by a housing of an internal component, the spatial separation being along a thickness of the housing, wherein
   an insulated wire arranged to connect the external coil to a hermetically sealed electronic circuitry comprised within the housing;
an external component comprising a microphone adapted to receive an audio sound and generate an electrical signal corresponding to the audio sound, a signal processor adapted to process the electrical signal for generating a processed electrical signal, and a transmitter coil adapted to inductively transmit the processed electrical signal to the receiver coil assembly; and
an implanted hermetically sealed electronic circuitry adapted to receive the processed electrical signal using the receiver coil assembly and generating stimulating electrical signals for an electrode array positioned within cochlea of a patient.

8. The cochlear implant according to claim 7, wherein the insulated wire follows shape of the housing by running from the external coil along an inner periphery, corresponding to thickness of the housing, to the hermetically sealed electronic circuitry.

9. The cochlear implant according to claim 8, wherein the inner periphery, along its thickness, comprises a groove path comprising a depth such that the insulated wire, running within the groove path, is flush with surface of the inner periphery.

10. The cochlear implant according to claim 7, wherein one of the external coil or the internal coil is adapted to receive energy from a transmitter coil connected to a power supply; and
another of the external coil or the internal coil is adapted to receive data from a transmitter coil connected to a data source.

11. The cochlear implant according to claim 7, wherein
the receiver coil assembly is adapted to be implanted within a patient and is adapted to be coupled to an implanted battery, the implantable battery being adapted to provide application specific energy;
the receiver coil assembly is connected to the hermetically sealed electronic circuitry adapted to determine charge level of the implanted battery and to initiate a charging stage if the determined charge level drops below a predetermined threshold value; and
during charging stage of the implanted battery, both the external coil and internal coil are adapted to receive energy from a transmitter coil connected to an external power supply and to provide the received energy for charging the implanted battery.

12. A cochlear implant comprising:
an implantable receiver coil assembly comprising:
   an external coil and an internal coil, the external coil and the internal coil being spatially separated coil units and comprised by a housing of an internal component, the spatial separation being along a thickness of the housing, wherein
   an insulated wire to connect the external coil to a hermetically sealed electronic circuitry comprised within the housing;
an external component comprising a microphone adapted to receive an audio sound and generate an electrical signal corresponding to the audio sound, and a transmitter coil adapted to inductively transmit the electrical signal to the receiver coil assembly; and
an implantable hermetically sealed electronic circuitry adapted to receive the electrical signal using the receiver coil assembly, to process the received electrical signal for generating a processed electrical signal and generating stimulating electrical signals for an electrode array positioned within cochlea of a patient.

13. A cochlear implant comprising:
an implantable receiver coil assembly comprising:
an external coil and an internal coil, the external coil and the internal coil being spatially separated coil units and comprised by a housing of an internal component, the spatial separation being along a thickness of the housing, wherein
an insulated wire arranged to connect the external coil to a hermetically sealed electronic circuitry comprised within the housing, wherein
the external coil is adapted to receive data information corresponding to high frequency sound information, and
the internal coil is adapted to receive data information corresponding to low frequency sound information.

14. The cochlear implant according to claim 12, wherein the insulated wire follows shape of the housing by running from the external coil along an inner periphery, corresponding to thickness of the housing, to the hermetically sealed electronic circuitry.

15. The cochlear implant according to claim 14, wherein the inner periphery, along its thickness, comprises a groove path comprising a depth such that the insulated wire, running within the groove path, is flush with surface of the inner periphery.

16. The cochlear implant according to claim 12, wherein one of the external coil or the internal coil is adapted to receive energy from a transmitter coil connected to a power supply; and
another of the external coil or the internal coil is adapted to receive data from a transmitter coil connected to a data source.

17. The cochlear implant according to claim 12, wherein the receiver coil assembly is adapted to be implanted within a patient and is adapted to be coupled to an implanted battery, the implantable battery being adapted to provide application specific energy;
the receiver coil assembly is connected to the hermetically sealed electronic circuitry adapted to determine charge level of the implanted battery and to initiate a charging stage if the determined charge level drops below a predetermined threshold value; and
during charging stage of the implanted battery, both the external coil and internal coil are adapted to receive energy from a transmitter coil connected to an external power supply and to provide the received energy for charging the implanted battery.

18. The cochlear implant according to claim 13, wherein the insulated wire follows shape of the housing by running from the external coil along an inner periphery, corresponding to thickness of the housing, to the hermetically sealed electronic circuitry.

19. The cochlear implant according to claim 18, wherein the inner periphery, along its thickness, comprises a groove path comprising a depth such that the insulated wire, running within the groove path, is flush with surface of the inner periphery.

20. The cochlear implant according to claim 13, wherein one of the external coil or the internal coil is adapted to receive energy from a transmitter coil connected to a power supply; and
another of the external coil or the internal coil is adapted to receive data from a transmitter coil connected to a data source.

* * * * *